(12) United States Patent
Miura et al.

(10) Patent No.: US 6,951,640 B2
(45) Date of Patent: Oct. 4, 2005

(54) USE OF NOVEL METALLOPORPHYRINS AS IMAGEABLE TUMOR-TARGETING AGENTS FOR RADIATION THERAPY

(75) Inventors: Michiko Miura, Hampton Bays, NY (US); Daniel N. Slatkin, Southold, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 286 days.

(21) Appl. No.: 10/375,454

(22) Filed: Feb. 27, 2003

(65) Prior Publication Data

US 2003/0165426 A1 Sep. 4, 2003

Related U.S. Application Data

(63) Continuation-in-part of application No. 09/874,203, filed on Jun. 6, 2001, now Pat. No. 6,566,517.

(51) Int. Cl.⁷ ............................ A61K 51/00; C07F 5/00; A01N 55/02
(52) U.S. Cl. ...................... 424/1.65; 424/1.85; 534/10; 534/14; 534/15; 514/185
(58) Field of Search ................ 424/1.65, 1.85, 424/9.3, 9.363; 540/145; 534/10, 14, 15; 514/185

(56) References Cited

U.S. PATENT DOCUMENTS

| | | | | |
|---|---|---|---|---|
| 5,877,165 A | * | 3/1999 | Miura et al. .................. 514/64 |
| 6,566,517 B2 | * | 5/2003 | Miura et al. ................. 540/145 |
| 6,759,403 B2 | * | 7/2004 | Miura et al. ................. 514/185 |

* cited by examiner

Primary Examiner—Michael Hartley
(74) Attorney, Agent, or Firm—Margaret C. Bogosian

(57) ABSTRACT

The present invention covers halogenated derivatives of boronated phorphyrins containing multiple carborane cages having the formula

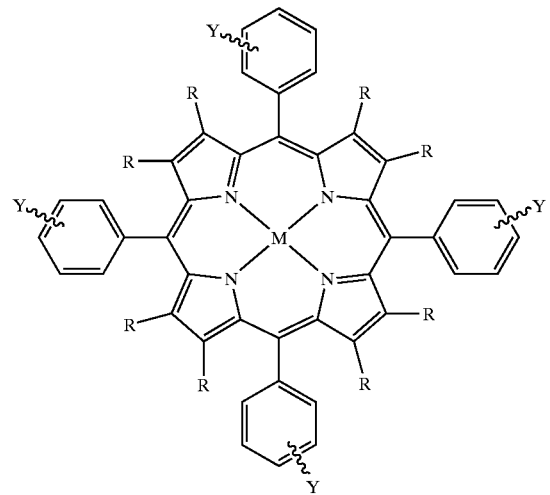

which selectively accumulate in neoplastic tissue within the irradiation volume and thus can be used in cancer therapies including, but not limited to, boron neutron-capture therapy and photodynamic therapy. The present invention also covers methods for using these halogenated derivatives of boronated porphyrins in tumor imaging and cancer treatment.

13 Claims, 1 Drawing Sheet

USE OF NOVEL METALLOPORPHYRINS AS IMAGEABLE TUMOR-TARGETING AGENTS FOR RADIATION THERAPY The present application is a continuation-in-part of U.S. patent application Ser. No. 09/874,203 filed on Jun. 6, 2001 now U.S. Pat. No. 6,566,517 incorporated herein by reference.

This invention was made with Government support under contract number DE-AC 02-98CH10886, awarded by the U.S. Department of Energy. The Government has certain rights in the invention.

BACKGROUND OF THE INVENTION

The present invention relates to compounds and methods for treating malignant tumors, in particular brain tumors and tumors of the head and neck, using such compounds.

Porphyrins in general belong to a class of colored, aromatic tetrapyrrole compounds, some of which are found naturally in plants and animals, e.g., chlorophyll and heme, respectively. Porphyrins are known to have a high affinity to neoplastic tissues of mammals, including man. Because of their affinity for neoplastic tissues, in general, porphyrins with boron-containing substituents could prove useful in the treatment of primary and metastatic tumors of the central nervous system by boron neutron capture therapy (BNCT). Porphyrins and other tetrapyrroles with relatively long singlet lifetimes have already been used to treat malignant tumors with photodynamic therapy (PDT), but this application has limited clinical applicability because of the poor penetration of the visible light required to activate the administered enhancer so as to render it toxic to living tissues, i.e., to the targeted tumor.

Porphyrins have the added potential advantage of being useful in vivo as chelating agents for certain paramagnetic metal ions to achieve higher contrast in magnetic resonance imaging (MRI). They could also be chelated with radioactive metal ions for tumor imaging in single-photon-emission computed tomography (SPECT) or position emission tomography (PET). In principle, porphyrins could also be used for high-specific-activity radioisotope therapy when the carrier molecule can be targeted with sufficient biospecificity to the intended lesion so as to avoid normal tissue radiotoxicity, which is most often encountered, when present at all, in the bladder, bone marrow, liver, and lung—the likely sites of undesired bioaccumulation of unbound carrier or its degradation products.

Boron neutron-capture therapy (BNCT) is a bimodal cancer treatment based on the selective accumulation of a $^{10}B$ carrier in tumors and subsequent irradiation with thermalized neutrons. The production of microscopically localized high linear-energy-transfer (LET) radiation from capture of thermalized neutrons by $^{10}B$ in the $^{10}(n, \alpha)^7Li$ reaction is responsible for the high efficacy and sparing of normal tissues. More specifically, the stable nuclide $^{10}B$ absorbs a thermalized neutron to create two mutually recoiling ionizing high-energy charged particles, $^7Li$ and $^4He$, with microscopic ranges of 5 $\mu$m and 9 $\mu$m, respectively.

When BNCT is used to treat patients experimentally with malignant tumors, the patient is given a boron compound highly enriched ($\approx$95 atom %) in boron-10. The boronated compound is chosen based on its ability to concentrate preferentially in the tumor within the radiation volume. In the case of brain tumors, after injection of the boron compound, the patient's head is irradiated in the general area of the brain tumor with an incident beam or field of epithermal (0.5 eV–10 keV) neutrons. These neutrons become progressively thermalized (average energy approximately 0.04 eV) as they penetrate deeper into the head. As the neutrons become thermalized, they can more readily be captured by the boron-10 concentrated in the tumor cells and/or tumor supporting tissues, since the capture cross section is inversely proportional to the neutron velocity. A minuscule proportion of the boron-10 nuclei in and around a tumor undergoes a nuclear reaction immediately after capturing a neutron, which is why such a large concentration of boron-10 is required in and/or around a targeted cell or tissue for BNCT to be clinically effective. The present invention, when implemented clinically alone or in combination with existing or other new therapies, will meet this 'high-concentration without undue toxicity' requirement better than previously known compounds. This nuclear reaction produces the high linear energy transfer (LET) alpha ($^4He$) and lithium ($^7Li$) particles. The tumor in which the boron-10 is concentrated is irradiated by these short range particles which, on average, travel a distance comparable to, or slightly less than, the diameter of a typical tumor cell. Therefore, a very localized, specific reaction takes place whereby the tumor receives a large radiation dose compared with that received by surrounding non-neoplastic tissues, with relatively low boron-10 concentrations.

For BNCT of malignant brain tumors, it is particularly important that there be robust uptake of boron in tumor relative to normal tissues (i.e., blood and normal brain tissues) within the neutron-irradiated target volume. BNCT was used clinically at the Brookhaven National Laboratory Medical Department with p-boronophenylalanine (BPA) as the boron carrier (Chanana et al., *Neurosurgery*, 44, 1182–1192, 1999). BPA has the outstanding quality of not eliciting any chemical toxicity associated with its usage. However, because the brain and blood boron concentrations are approximately one-third those found in tumor, the tumor dose is restricted. In order to improve upon the currently used boron delivery agent, BPA, it has been postulated that tumor boron concentrations should be greater than 30 $\mu$g B/g and tumor:blood and tumor:brain boron ratios should be greater than 5:1 (Fairchild and Bond, *Int. J. Radiat. Oncol. Biol. Phys.*, 11, 831–840, 1985, Miura, et al., *Int. J. Cancer*, 68, 114–119, 1996).

In PDT of malignant tumors using porphyrins, the patient is injected with a photosensitizing drug. The drug localizes preferentially in the tumor within the irradiation volume.

The patient's tissues in the zone of macroscopic tumor is then irradiated with a beam of red laser light. The vascular cells of the irradiated tumor and some of the tumor cells are rendered incapable of further mitotic activity or may be killed outright if the light penetrates the tissue sufficiently. The biochemical mechanism of cell damage in PDT is believed to be mediated largely by singlet oxygen. Singlet oxygen is produced by transfer of energy from the light-excited porphyrin molecule to an oxygen molecule. The resultant singlet oxygen is highly reactive chemically and is believed to react with and disable cell membranes. Macroscopically, there appear to be some direct damage to tumor cells, extensive damage to the endothelial cells of the tumor vasculature, and infiltration of the tumor by macrophages. The macrophages remove detritus of dead cells from the PDT-treated zones of tissue, and in the process, are believed to damage living cells also.

In PDT, the drugs must be selectively retained by tumors, especially within the irradiation volume. However, the drugs should be non-toxic or minimally toxic when administered in therapeutically useful doses. In addition, drugs with absorbance peaks at long wavelengths allow increased tissue penetration and, thereby, allow photoablation of some or all of the vasculature and/or the parenchyma of deeper-seated tumors.

While it is well known in medical arts that porphyrins have been used in cancer therapy, there are several criteria that must be met for a porphyrin-mediated human cancer radiation treatment to be optimized. In BNCT, the porphyrin drug should deliver a therapeutically effective concentration of boron to the tumor while being minimally toxic to normal vital tissues and organs at a radiotherapeutically effective pharmacological whole-body dose of porphyrin. In addition, the porphyrin should have selective affinity for the tumor with respect to its affinity to surrounding normal tissues within the irradiation volume, and should be capable of achieving tumor-to-normal-tissue boron concentration ratios greater than 5:1. In vivo studies have shown that the latter criterion can be satisfied for brain tumors if the porphyrin, properly designed, synthesized and purified, does not penetrate the blood-brain barrier in non-edematous zones of the normal CNS.

In addition, if the boron concentration and distribution in and around the tumor can be accurately and rapidly determined noninvasively, BNCT treatment planning can be more quickly, accurately, and safely accomplished. For example, neutron irradiation could be planned so that concurrent boron concentrations are at a maximum at the growing margin of the tumor rather than in the tumor as a whole. Thus, BNCT could be implemented by one relatively short exposure or by a series of short exposures of mainly epithermal neutrons, appropriately timed to take advantage of optimal boron concentrations identified by SPECT or MRI in tumor, surrounding tissues, and blood in vivo. BNCT effectiveness in vivo is probably not diminished even when a neutron exposure is as short as 300 milliseconds. Such short irradiations have been delivered effectively, in fact, by a TRIGA (General Atomics) reactor operating in the pulse mode. Mice bearing advanced malignant sarcomas transplanted subcutaneously in the thigh were palliated and in many cases cured by BNCT using 300 millisecond 'pulse' exposures to slow neutrons (Farr, L. E., BNL Report No. 47087, 1992). Short irradiations would obviate the inconvenience and discomfort to the patient of long and often awkward positioning of the head at a reactor port. This advantage alone would justify a clinical use for BNCT, if palliative results on the tumor were at least as favorable as those following the presently, available standard, 6-week, 30-fraction postoperative linear-accelerator-based photon radiation therapy.

Efforts have been made to synthesize porphyrins for the diagnosis, imaging and treatment of cancer. In U.S. Pat. No. 4,959,356 issued to Miura, et al. (which is incorporated herein in its entirety), a particular class of porphyrins was synthesized for utilization in the treatment of brain tumors using BNCT. The porphyrins described in that patent are natural porphyrin derivatives which contain two carborane cages at the 3 and 8 positions. Natural porphyrins have particular substitution patterns which are, in general, pyrrole-substituted and asymmetric. The porphyrins described in U.S. Pat. No. 4,959,356 use heme, the iron porphyrin prosthetic group in hemoglobin, as a chemical starting material; therefore, the resulting boronated porphyrins resemble heme in their basic structure. In contrast, the porphyrins of the current invention are synthetic tetraphenylporphyrin (TPP) derivatives that are symmetrically substituted at the methine positions. Most are also substituted at the pyrrole positions of the macrocycle. Acyclic precursors are used as chemical starting materials so that final product yields are generally greater than those obtained from natural porphyrin derivatives.

U.S. Pat. No. 5,877,165 issued to Miura et al. (which is incorporated herein in its entirety) is focused on boronated tetraphenyl porphyrins containing multiple carborane cages which selectively accumulate in neoplastic tissue and which can be used in cancer therapies such as boron neutron capture and photodynamic therapy.

U.S. Pat. Nos. 5,284,831 and 5,149,801 issued to Kahl, et al. describe another type of porphyrin and their uses in BNCT, PDT and other biomedical applications. Like the porphyrins described in the previous patent by Miura et al., these are also natural porphyrin derivatives but they contain four carborane cages at the 3 and 8 positions.

U.S. Pat. No. 4,500,507 issued to Wong describes a method of labeling hematoporphyrin derivatives (HPD) with $^{99m}Tc$ as a means of visualizing tumors using scintigraphic noninvasive imaging techniques such as SPECT. The method taught by this patent utilizes hematoporphyrin compounds that are also natural porphyrin derivatives.

U.S. Pat. No. 4,348,376 to Goldenberg, U.S. Pat. No. 4,665,897 to Lemelson, and 4,824,659 to Hawthorne teach combining labeling of an antibody with $^{10}B$ and with one or more other radionuclides, including those of iodine, for purposes of imaging tumors noninvasively and thereby delineating tumor targets for exposure to thermalized neutrons. Each of these patents requires that the $^{10}B$ compound be linked to a radiolabeled antibody.

Improvement in the efficacy of conventional radiotherapy using chemical agents is a key area of interest in experimental radiation oncology. Currently, more than 750,000 patients in the U.S. receive photon radiation therapy for cancer per year. Success has been limited due to restriction of the tumor dose to avoid critical normal tissue morbidity. Hypoxic cells in tumor can be a major problem because they are three times less sensitive to photon radiation than oxygenated cells. While a whole range of hypoxic cell radiation sensitizing agents have been developed, most have proven clinically ineffective. Accordingly, there is a need for effective hypoxic cell radiation sensitizing agents.

SUMMARY OF THE INVENTION

The present invention relates to porphyrin compounds of the formula

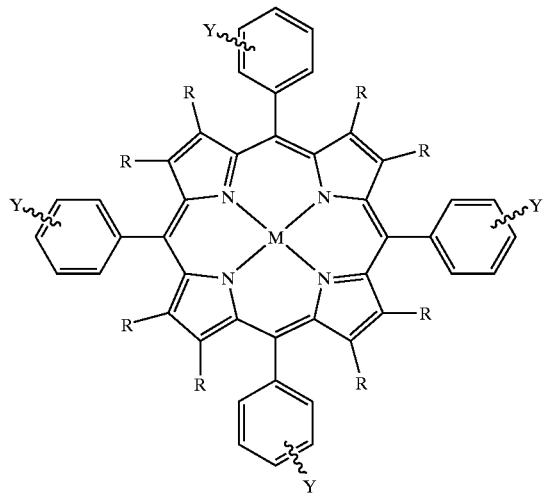

wherein M is a single-photon-emission tomography (SPECT) imageable radiometal and/or a paramagnetic metal, at least one R is a halogen (fluorine, chlorine, bromine, astatine or iodine), a halogen isotope or a nitro group, and Y is selected from the group consisting of ortho, meta, or para $O(CH_2)_nC_2HB_9H_{10}$ or $O(CH_2)_nC_2HB_{10}H_{10}$ wherein, $0 \leq n \leq 20$ and $C_2HB_9H_{10}$ is nido ortho, meta- or para-carborane and $C_2 HB_{10}H_{10}$ is ortho-carborane, meta-carborane or para-carborane. M can be selected from the group consisting of vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), and gadolinium (Gd). The most preferred metals are Cu and Ni. In a preferred embodiment, R is a halogen (F, Cl, Br, I, At), most preferably bromine, a bromine isotope, iodine or an iodine isotope. In another embodiment, R is from one to seven hydrogen. Y is preferably $OCH_2C_2HB_9H_{10}$, wherein $C_2HB_9H_{10}$ is nido-ortho-carborane or $OCH_2C_2HB_{10}H_{10}$, wherein $C_2HB_{10}H_{10}$ is ortho-carborane. In another embodiment, R is fluorine, chlorine, bromine, iodine, astatine, a nitro group a combination thereof or a combination thereof that includes a hydrogen.

In one embodiment of the present invention, the porphyrin compounds have the formula

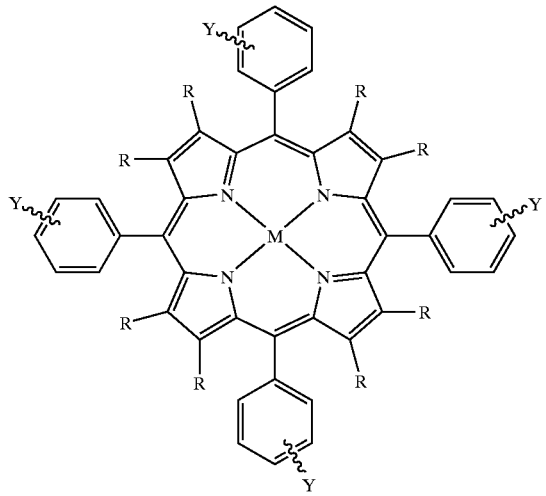

wherein M is a single-photon-emission tomography (SPECT) imageable radiometal and/or a paramagnetic metal, R is fluorine, a fluorine isotope, chlorine, a chlorine isotope, bromine, a bromine isotope, iodine, an iodine isotope, astatine, an astatine isotope, a nitro group, a combination thereof or a combination thereof that includes hydrogen and Y is selected from the group consisting of ortho, meta, or para $O(CH_2)_nC_2HB_9H_{10}$ or $O(CH_2)_nC_2HB_{10}H_{10}$, wherein, $0 \leq n \leq 20$ and $C_2HB_9H_{10}$ is nido ortho, meta- or para-carborane and $C_2HB_{10}H_{10}$ is ortho-carborane, meta-carborane or para-carborane. M is selected from the group consisting of V, Mn, Fe, Ru, Tc, Cr, Pt, Co, Ni, Cu, Zn, Ge, In, Sn, Y, Au, Ba, W, and Gd. In a preferred embodiment, Y is preferably $OCH_2C_2HB_9H_{10}$, wherein $C_2HB_9H_{10}$ is nido-ortho-carborane or $OCH_2C_2HB_{10}H_{10}$, wherein $C_2HB_{10}H_{10}$ is ortho-carborane.

The present invention also includes a method of tumor imaging and a method of bimodal cancer treatment that includes the administration to a subject of a composition that contains one or more of the porphyrin compounds described above. In a preferred embodiment, the composition is essentially the one or more of the porphyrin compounds.

Because porphyrins of the present invention have electron-withdrawing groups at the periphery of the macrocycle the reduction potentials are more positive than those with hydrogen or alkyl groups. Such electrochemical properties are believed to be desirable for radiosensitizers in photon radiotherapy (R. A. Miller et al., Int. J. Radiat. Oncol. Biol Phys., 45, 981–989, 1999). Coupled with their biodistribution and toxcicological properties, porphyrins of the present invention are believed to have potential as effective radiosensitizers.

BRIEF DESCRIPTION OF THE FIGURES

Other objects and many attendant features of this invention will be readily appreciated as the invention becomes

DETAILED DESCRIPTION OF THE INVENTION

Figure 1:
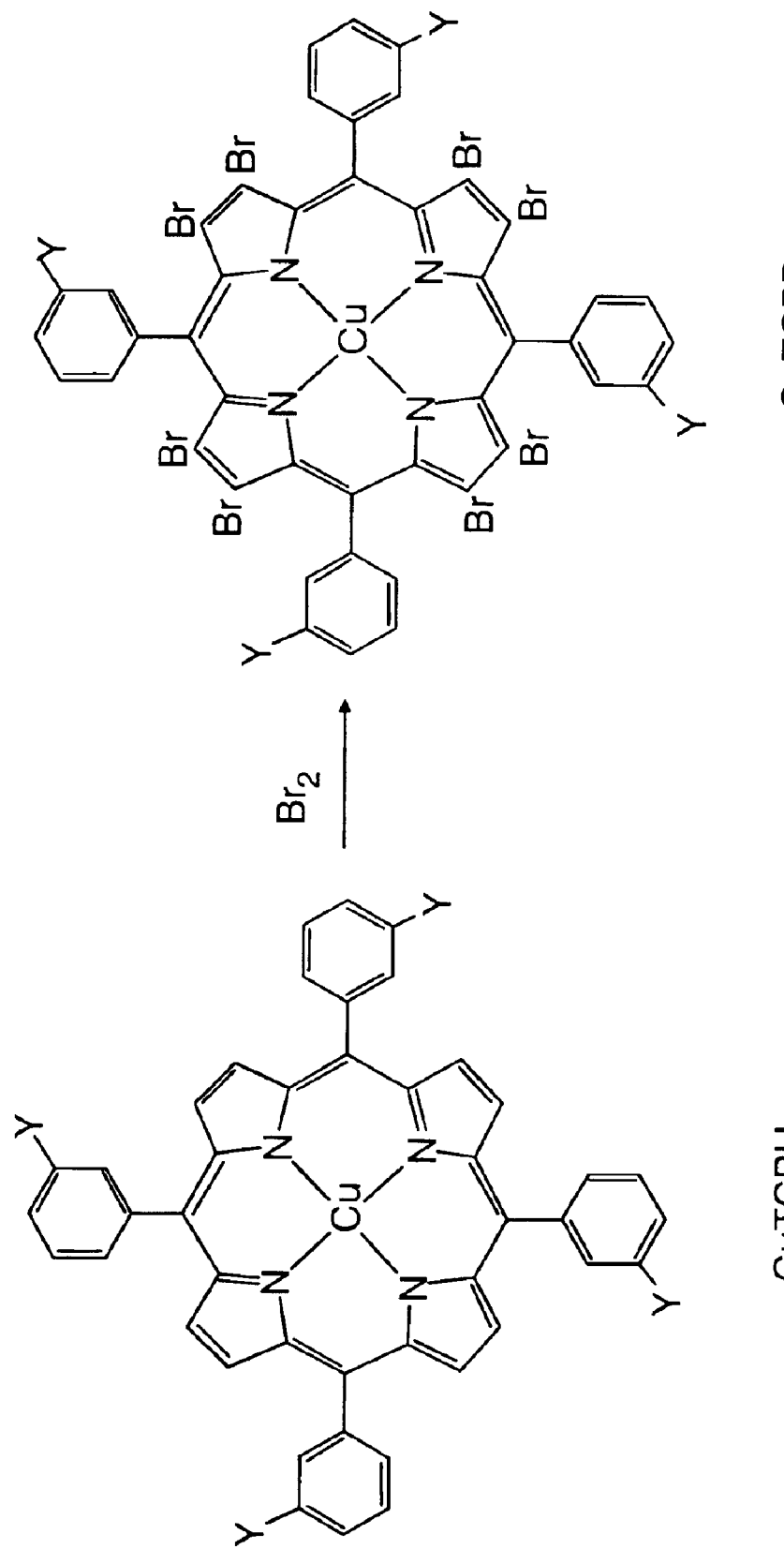
FIG. 1 shows the synthesis of CuTCPBr from CuTCPH.

The present invention relates to halogenated (i.e., fluorinated, chlorinated, brominated, iodinated, and, conceivably, astatinated), and nitrated tetraphenylporphyrins and their use as imageable tumor-targeting agents for ionizing and/or non-ionizing radiation therapy. The halogenated tetraphenylporphyrins are synthesized from carborane-containing tetraphenylporphyrins. The halogenated tetraphenylporphyrins of the present invention are octahalogen analogs of the carborane-containing tetraphenylporphyrins and are prepared by synthesizing the carborane-containing tetraphenylporphyrins with a halogen in a solvent mixture such as chloroform and carbon tetrachloride.

CuTCPH and CuTCP, two carborane-containing tetraphenylporphyrins, have been found to deliver high concentrations of boron to various tumors in animals. In addition, it has recently been found that CuTCPH-mediated BNCT can control a considerable percentage of animal tumors with little normal tissue damage. In one embodiment of the present invention, CuTCPH is brominated to form CuTCPBr, an octa-bromo analog, which has biodistribution and toxicological properties similar to those of CuTCP in mice bearing EMT-6 mammary carcinomas. Such brominated porphyrins are easier to reduce than their bromine-free precursors. It is believed that the low reduction potential of a larger macrocycle, texaphyrin, is responsible for its high in vivo efficacy as a tumor-selective radiosensitizer during photon-based radiotherapy of tumors. However, CuTCPBr has a major practical advantage over the texaphyrins for BNCT because its tumor:normal brain and tumor:blood concentration ratios are 100:1 vs. 10:1 for the texaphyrins.

FIG. 1 shows the synthesis of CuTCPBr from CuTCPH using a bromination procedure that includes dissolving CuTCPH in a 1:1 solvent mixture of chloroform and carbon tetrachloride. While the mixture is stirred, bromine in the same solvent mixture is added. Pyridine in a solvent mixture is then added and constantly stirred at room temperature. The excess bromine is then quenched with an aqueous sodium metabisulfite solution. The reaction mixture is formed by extracting the organic layer and washing with water. The organic layer is then dried and the solvents removed.

Similarly, CuTCPCl is formed using N-chlorosuccinimide as the chlorinated agent and CuTCPI is formed using a similar iodinating reagent. Hepta- and octa-nitro porphyrins can be synthesized using nitric acid and acetic anhydride in the presence of K10 montmorillonite. The beta-substituted fluoroporphyrins cannot be synthesized by fluorination of beta-free porphyrins, but must be synthesized using 3,4 difluoropyrrole as a starting material for the porphyrin cyclization.

The halogenated tetraphenylporphyrins of the present invention can also be synthesized using isotopes of the different halogens. The preferred isotopes are Br-76 with a half life ($T_{1/2}$) of 16 hours, Br-77 ($T_{1/2}$=57 hours), I-124 ($T_{1/2}$=101 hours), I-131 ($T_{1/2}$=192 hours), F-18 ($T_{1/2}$=110 minutes), and At-211 ($T_{1/2}$=7.214 hours).

CuTCPBr and the hepta- and octa-nitrotetraphenylporphyrins have a range of reduction potentials that encompasses that of the texaphyrins. The examples that follow show the effectiveness of the biodistribution properties of these compounds in tests conducted using mice bearing EMT-6 carcinomas.

Photoactivation can be somewhat amplified by tuning much of the X-ray energy to that above the K-edge of either the metal or the halogen. The K-edge is determined by the interaction of the K-shell electron with the nucleus of the atom and it is unique for each element. Each element has its own unique K-shell binding energy. $^{64}$Cu, $^{18}$F and $^{76}$Br are isotopes available for quantitative positron-emission tomography (PET). The $^{64}$Cu and $^{76}$Br can be attached to the tetraphenylporphyrins at a late stage in the synthesis. These isotopic substitutions could greatly improve treatment planning for any future clinical applications of CuTCPBr or its analogs, since local concentrations of the radioactive isotope could then be visualized and quantified voxel by voxel, thereby enabling calculation of the boron concentration in the brain, head, neck or in another targeted organ or tissue of interest, voxel by voxel.

The porphyrin compounds of the present invention that have been tested in vivo are non-toxic at potentially therapeutic doses. Implementation of BNCT and/or PDT in animals and patients so dosed could selectively destroy tumor tissue without disruption of normal tissue function when irradiated with epithermal neutrons or laser light. The tumor destruction could occur without the serious side effects that may be observed in conventional tumor therapy, such as radiotherapy or chemotherapy.

To accumulate the requisite amount of a compound of the present invention in a tumor for BNCT, generally a systemically injected or infused dose of about 100–400 mg halogenated tetraphenylporphyrin compound per kg body weight in a pharmaceutically acceptable carrier is administered to a patient. Such a carrier could include liposomes and/or commercially available solvents, such as Cremophore EL, propylene glycol, Tween 80 and the like. The compound is administered in one or more doses, the last dose being given between about one hour and one week prior to the epithermal or thermal, for superficial tumors, neutron irradiation. The long retention time of any of the presently invented compounds would also permit a series of such irradiations in a so-called "fractionated irradiation schedule." Such a schedule is deemed to be advantageous in sparing damage to normal tissues in conventional photon radiation therapy. The quantity of the halogenated tetraphenylporphyrin used in any particular treatment depends on, among other factors, the boron concentration delivered to the tumor and the toxicity of the compound at doses that are therapeutically useful.

The timing of the neutron exposure depends upon the concentration of the boron in blood, which decreases more rapidly with time than does the tumor boron concentration. The timing of the administration of the halogenated tetraphenylporphyrin depends on various considerations. Important considerations are the pharmacokinetic behavior of the compound, (e.g., the rate of absorption of the compound into the tumor and into the tumor vasculature) and the rate of excretion from and/or metabolism of the compound in the various tissues that absorb the compound in the patient.

It has long been known that porphyrins accumulate robustly in many kinds of tumors as well as in a few non-tumorous tissues. In human cancer therapy, this property has been used only for photodynamic therapy (PDT) to date. However, pre-clinical research is active in developing carboranyl derivatives of porphyrins for boron neutron-capture therapy (BNCT).

In an embodiment of the present invention, brominated carboranylporphyrins are synthesized to provide an imageable nuclide in a porphyrin that can also be used to image a tumor non-invasively. Since the ratio of the imageable nuclide to the boron is invariant if the administered boronated compound is substantially chemically stable in vivo, quantification of the imaged nuclide, voxel by voxel, provides real-time quantification of the boron, voxel by voxel. This greatly enhances the treatment planning for clinical porphyrin-based BNCT and therefore adds to the potential advantage of the high tumor boron concentrations already demonstrated by some carboranyl porphyrins. An example of such a metalloporphyrins is copper octabromotetracarboranylphenylporphyrin. The bromine can be $^{76}$Br ($T_{1/2}$=16 hrs), which is imageable by positron-emission tomography (PET) or $^{77}$Br ($T_{1/2}$=57 hrs), which is imageable by single-photon emission computed tomography (SPECT). In another embodiment, iodine is substituted for bromine and PET and SPECT can be used with $^{124}$I and $^{131}$I respectively. In addition, non-radioactive natural abundance iodine-can be used with spiral "ultra fast" computed tomography (CT) to localize and quantify tumor boron rapidly by employing the iodine component of CuTCPI as a radiographic contrast-enhancing element.

The reduction potential of the porphyrin macrocycle becomes more positive (i.e., more easily reduced) with the addition of electron-withdrawing groups such as bromine. The first reduction potential $E_{1/2}$ for copper tetraphenylporphyrin (CuTPP) is −1.2 V, whereas that for copper octabromotetraphenylporphyrin (CuOBP) is −0.59 V. The meta-substituted carboranylmethoxy group on the phenyl moiety of copper tetracarboranylmethoxyphenylporphyrin (CuTCPH) is not expected to affect the reduction potential. Accordingly, the $E_{1/2}$ for the octabromo derivative of CuTCPH (i.e., CuTCPBr) is estimated to be approximately −0.59 V.

The radiation-enhancement properties of gadolinium texaphyrins are attributed to their relatively large reduction potentials, −0.04 V. However, reduction potentials that are optimal for radiotherapy have not yet been established. The eight bromo groups in CuTCPBr provide moderately strong electron-withdrawing groups to the tetraphenylporphyrin structure. If more positive reduction potentials are required for greater efficacy in the control of neoplastic tissues, groups with greater electron-withdrawing properties such as fluoro or nitro groups can be used in place of the bromo substituents.

Tests in animals have shown that the carboranylporphyrins of the present invention provide low toxicity and high tumor accumulation of the described porphyrins. In addition, the carboranylporphyrins of the present invention can be used in a variety of cancer treatment modalities and they are imageable by a number of different methods.

EXAMPLE 1

In this example, CuTCPBr was synthesized from CuTCPH by a bromination procedure. CuTCPH (200 mg, 0.146 mmol) was dissolved in a 1:1 solvent mixture of chloroform and carbon tetrachloride (70 mL). While the mixture was being stirred, bromine (240 µL, 4.6 mmol) in the same solvent mixture 20 mL) was added over a period of 30 min. Pyridine (0.6 mL) in a solvent mixture (15 mL) was added over 30 min and then left overnight at room temperature with constant stirring. The next morning the excess bromine was quenched with an aqueous 20% sodium metabisulfite solution (40 mL). The reaction mixture was worked up by extracting the organic layer and washing 3 times with water. The organic layer was then dried over anhydrous sodium sulfate and the solvents removed in vacuo. The desired product was purified by preparative thin layer chromatography. The yield was 176 mg (0.088 mmol) which is about 60%.

The compound was characterized by optical absorption and infrared spectroscopies, fast-atom bombardment mass spectral analysis, and elemental analysis. The NMR was difficult to interpret because of the presence of copper, a paramagnetic metal. The optical spectrum showed a pattern consistent with octabromination of the starting porphyrin. The Soret band shifted from 415 to 440 nm and the visible band shifted from 540 to 580 nm. A mass spectrum showed a parent ion peak that matched the molecular weight of the compound at 1996. Elemental analysis: Calculated for $C_{56}H_{68}O_4B_{40}Br_8Cu$; C 33.69, H 3.43, N 2.81; Found C 33.65, H 3.62, N 2.43. FT-1R (KBr) 2582 cm$^{-1}$ (BH).

EXAMPLE 2

Carcinomas of the Dorsal Thorax

Five BALB/c mice bearing subcutaneously implanted EMT-6 mammary carcinomas on the dorsal thorax were given a total dose of 186 µg CuTCPBr/g body weight in 6 intraperitoneal (ip) injections over a period of 2 days. Four days after the last injection, mice were euthanized and the average boron concentrations (µg/g wet tissue) were measured for different types of tissue. The results are shown in Table 1.

TABLE 1

| TISSUE | µg B/g wet tissue |
| --- | --- |
| tumor | 84 ± 15 |
| blood | 0.6 ± 0.2 |
| brain | 0.5 ± 0.1 |
| liver | 272 ± 93 |

No toxic effects were noted either physically or behaviorally in the mice during and after porphyrin administration. At necropsy, all tissues appeared normal.

EXAMPLE 3

Human Gliomas on the Dorsal Thorax

In this example, severe combined immune-deficient (SCID) mice bearing xenografts of U373 human gliomas were given 180 µg CuTCPBr/gbw in a volume of 0.01 mL/gbw/injection over a period of 2 days. Mice were euthanized 2 days after the last injection and the results are shown in Table 2.

TABLE 2

| TISSUE | µg B/g wet tissue |
| --- | --- |
| U373 Tumor | 81 ± 34 |
| Blood | 1.0 ± 0.3 |
| Cerebrum | 0.1 ± 0.1 |
| Ears | 7.6 ± 2.1 |
| Liver | 356 ± 68 |

EXAMPLE 4

Carcinomas of the Leg

In this example, BALB/c mice bearing subcutaneous EMT-6 leg tumors were given 180 µg CuTCPBr/gbw in a volume of 0.01 mL/gbw/injection over a period of 2 days. Boron concentrations (μg/g) in various tissues from the BALB/c mice were measured at 2 days after the last injection and the results are shown in Table 3.

TABLE 3

| Days after last injection | No. mice | Tumor | Blood | Cerebrum | External Ear (Pinna) | Liver |
|---|---|---|---|---|---|---|
| 2 | 7 | 70 ± 29 | 9.0 ± 5.1 | 0.1 ± 0.1 | 9.5 ± 4.2 | 295 ± 75 |

The EMT-6 tumor values from Tables 1 and 3 are comparable. However, blood boron is higher at the 2-day time point. The tumor: blood boron concentration ratio of 7:1 is still significantly higher than those from the compounds currently used clinically.

In the tests shown above in Examples 2, 3, and 4, no toxic effects were noted either physically or behaviorally in the mice during and after porphyrin administration. At necropsy, all tissues appeared normal. Toxicity is the critical factor, and since no toxicity was observed, the dose can be increased further to achieve tumor boron concentrations higher than those in Examples 2, 3, and 4. For example, when the total dose of a carboranyl porphyrin, CuTCPH, was increased from 195 to 450 mg/kg body weight in Fischer 344 rats bearing subcutaneous 9L gliosarcomas, the tumor boron concentration increased from a median of 64 to 117 μg/g.

Thus, while there have been described the preferred embodiments of the present invention, those skilled in the art will realize that other embodiments can be made without departing from the spirit of the invention, which includes all such further modifications and changes as come within the true scope of the claims set forth herein.

What is claimed is:

1. A method of tumor imaging using single-photon-emission tomography(SPECT) wherein the tumor imaging agent administered to the subject is a pharmaceutically acceptable composition containing a compound of the formula

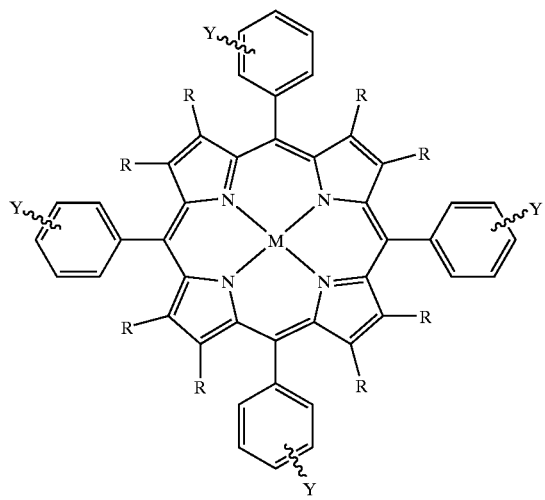

wherein M is a SPECT imageable radiometal with or without another carrier metal, R is selected from the group consisting of hydrogen, a halogen, a halogen isotope, or a nitro group, with at least one R being a halogen, a halogen isotope or a nitro group, and Y is selected from the group consisting of ortho, meta, or para $O(CH_2)_nC_2HB_9H_{10}$ or $O(CH_2)_nC_2HB_{10}H_{10}$ wherein, $0 \leq n \leq 20$ and $C_2HB_9H_{10}$ is nido ortho, meta- or para-carborane and $C_2HB_{10}H_{10}$ is ortho-carborane, meta-carborane para-carborane.

2. The method of claim 1, wherein at least one R is a halogen radioisotope.

3. The method of claim 2 wherein the halogen radio isotope is selected from the group consisting of $^{77}Br$, $^{123}I$, $^{125}I$, $^{131}I$, $^{209}At$, $^{210}At$, or $^{211}At$.

4. The method of claim 1, wherein M is selected from the group consisting of $^{67}Cu$, $^{99m}Tc$, and $^{111}In$.

5. A method of tumor imaging using positron emission tomography (PET) wherein the tumor imaging agent administered to the subject is a pharmaceutically acceptable composition containing a compound of the formula

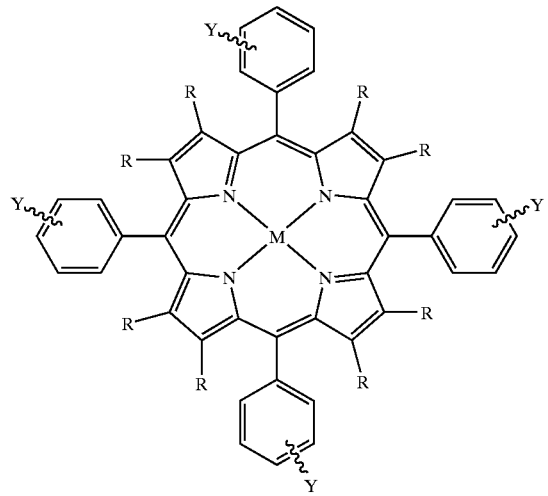

wherein M is a PET imageable radiometal with or without another carrier metal, R is selected from the group consisting of hydrogen, a halogen, a halogen isotope, or a nitro group, with at least one R being a halogen, a halogen isotope or a nitro group, and Y is selected from the group consisting of ortho, meta, or para $O(CH_2)_nC_2HB_9H_{10}$ or $O(CH_2)_nC_2HB_{10}H_{10}$ wherein, $0 \leq n \leq 20$ and $C_2HB_9H_{10}$ is nido ortho, meta-or para carborane and $C_2HB_{10}H_{10}$ is ortho-carborane, meta-carborane or para-carborane.

6. The method of claim 5 wherein M is $^{64}Cu$.

7. The method of claim 5 wherein at least one R is a halogen radioisotope.

8. The method of claim 7 wherein the halogen radioisotope is selected from the group consisting of $^{18}F$, $^{76}B$, $^{124}I$, $^{209}At$, $^{210}At$, and $^{211}At$.

9. A method of cancer treatment comprising:

administering tumor targeting agent to the subject, wherein the tumor targeting agent is a pharmaceutically acceptable composition containing a compound of the formula

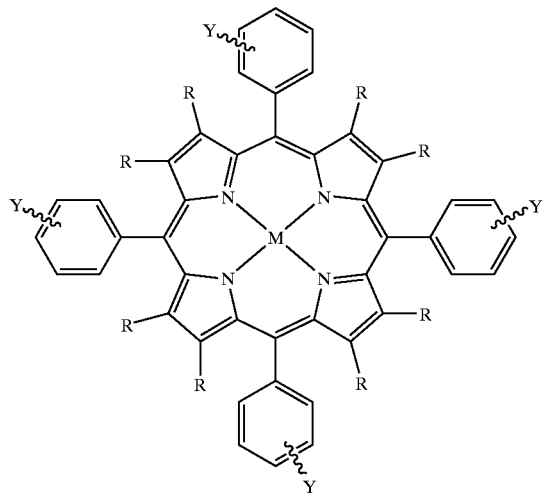

wherein M is a single-photon-emission tomography imageable radiometal or a paramagnetic metal, R is selected from the group consisting of hydrogen, a halogen, a halogen isotope, or a nitro group, with at least one R being a halogen, a halogen isotope or a nitro group, and Y is selected from the group consisting of ortho, meta, or para $O(CH_2)_nC_2HB_9H_{10}$ or $O(CH_2)_nC_2HB_{10}H_{10}$ wherein, $0 \leq n \leq 20$ and $C_2HB_9H_{10}$ is nido ortho, meta- or para-carborane and $C_2HB_{10}H_{10}$ is ortho-carborane, meta-carborane or para-carborane; and subsequently irradiating the tumor.

10. The method of claim 9 wherein R is bromine, a bromine isotope, iodine, an iodine isotope, chlorine, a chlorine isotope, fluorine, a fluorine isotope, astatine, an astatine isotope, a nitro group, a combination thereof, or a combination thereof that includes hydrogen.

11. The method of claim 9 wherein M is selected from the group consisting of vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), and gadolinium (Gd).

12. The method of claim 9 wherein the tumor is irradiated with thermalized neutrons for boron neutron capture therapy cancer treatment.

13. The method of claim 9 wherein the tumor is irradiated with a beam of red laser light for photodynamic therapy cancer treatment.

* * * * *